(12) United States Patent
Hedstrom et al.

(10) Patent No.: US 8,574,254 B2
(45) Date of Patent: Nov. 5, 2013

(54) ARTHROSCOPIC CUTTING BLADE

(75) Inventors: Petter A. Hedstrom, Haverhill, MA (US); Rafal Z. Jezierski, Middleton, MA (US); Kenneth W. Krause, Sandown, NH (US)

(73) Assignee: Smith & Nephew, Inc., Memphis, TN (US)

( * ) Notice: Subject to any disclaimer, the term of this patent is extended or adjusted under 35 U.S.C. 154(b) by 70 days.

(21) Appl. No.: 13/013,093

(22) Filed: Jan. 25, 2011

(65) Prior Publication Data

US 2012/0191119 A1 Jul. 26, 2012

(51) Int. Cl.
*A61B 17/32* (2006.01)

(52) U.S. Cl.
USPC .......................................... 606/171; 606/180

(58) Field of Classification Search
USPC ......... 606/159, 160, 170, 171, 175, 176, 178, 606/179, 180, 79; 604/22
See application file for complete search history.

(56) References Cited

U.S. PATENT DOCUMENTS

| | | | |
|---|---|---|---|
| 4,203,444 A | 5/1980 | Bonnell et al. | |
| 4,272,414 A | 6/1981 | Johnson et al. | |
| 4,834,729 A | 5/1989 | Sjostrom | |
| 4,842,578 A | 6/1989 | Johnson et al. | |
| 5,084,052 A * | 1/1992 | Jacobs | 606/170 |
| 5,320,635 A | 6/1994 | Smith | |
| 5,601,583 A * | 2/1997 | Donahue et al. | 606/170 |
| 5,709,698 A | 1/1998 | Adams et al. | |
| 6,217,598 B1 | 4/2001 | Berman et al. | |
| 6,419,684 B1 | 7/2002 | Heisler et al. | |
| 2005/0065538 A1 | 3/2005 | Van Wyk | |
| 2007/0282361 A1 | 12/2007 | Da Rold et al. | |
| 2008/0183201 A1 | 7/2008 | Berberich | |
| 2008/0208194 A1 | 8/2008 | Bickenbach | |
| 2010/0298855 A1 * | 11/2010 | Dierck | 606/170 |

FOREIGN PATENT DOCUMENTS

| | | |
|---|---|---|
| EP | 0800794 | 10/1997 |
| EP | 1690504 | 8/2006 |
| EP | 1698290 | 9/2006 |

* cited by examiner

*Primary Examiner* — Tuan V Nguyen
(74) *Attorney, Agent, or Firm* — Chapin IP Law, LLC

(57) ABSTRACT

A dual function arthroscopic blade provides multiple cutting surfaces of differing cut aggressiveness for selective engagement of the desired cutting blade without retracting the instrument for changing cutting members to apply a different set of cutting edges, or blade. An inner rotating member within a stationary outer cutting member provide cutting edges defined by cutting windows on the inner and outer cutting members, and a rotational drive applies an oscillating rotation such that one of the cutting windows, corresponding to one of the sets of cutting edges, engages an extraction region such as tissue or bone. The use of different sized cutting windows allows variance in the aggressiveness of the cut, and allows selection of another cutting window by rotating the cutting member to align the selected cutting edges without requiring extraction and reinsertion in order to attach a different blade with a different cut aggressiveness.

14 Claims, 12 Drawing Sheets

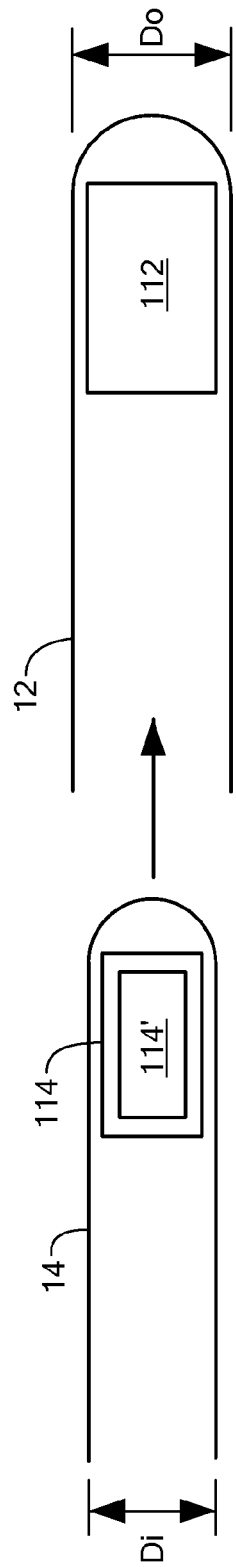
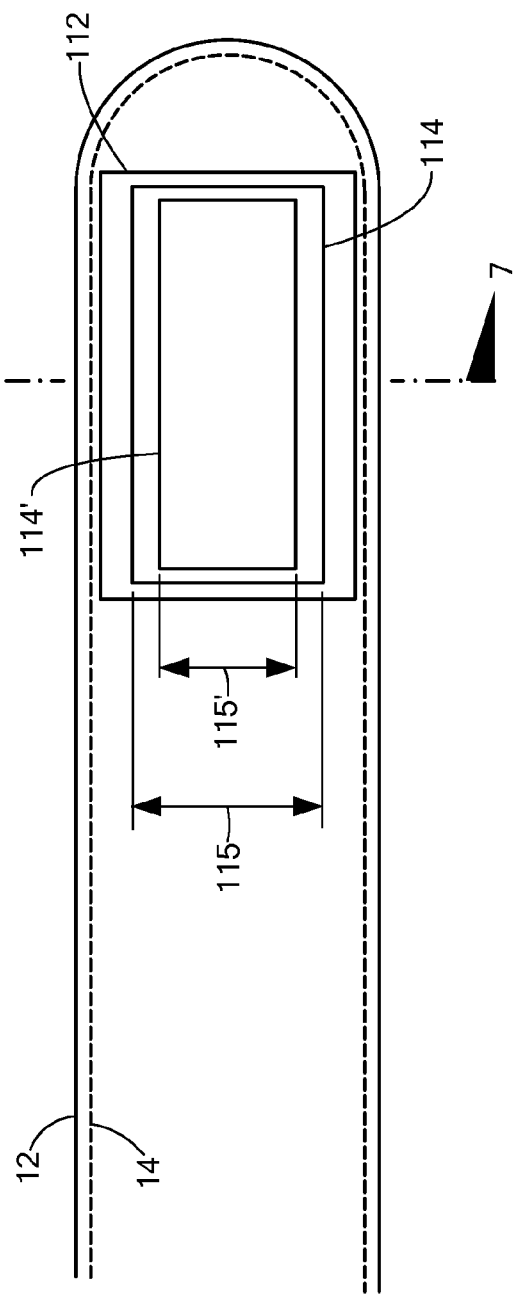
FIG. 5
FIG. 6

ARTHROSCOPIC CUTTING BLADE

BACKGROUND

Powered arthroscopic surgical instruments typically include a rigid, stationary outer tube within which a rigid inner tube is rotated by a motor. A cutting implement, such as a blade or abrading burr, is disposed on the distal end of the inner tube. Tissue or bone is exposed to the cutting implement through an opening in the distal end of the outer tube, and tissue or bone fragments cut by the rotating blade or burr are drawn through the interior of the inner tube along with irrigating fluid by the use of suction applied at the proximal end of the instrument.

A motorized attachment engages a hub, typically on the inner tube, and rotates the inner tube within the outer tube for providing cutting movement and force. The attachment also incorporates a suction attachment for evacuating cut matter from a surgical extraction site through the hollow tubes. Several surgical instruments of various complementary functions are often employed in a surgical field within a patient for performing surgical operations at the surgical site, one function of which is the controlled cutting and evacuation of tissue and bone fragments.

SUMMARY

A dual function arthroscopic blade provides multiple cutting surfaces of differing cut aggressiveness for selective engagement of the desired cutting blade without retracting the instrument for changing cutting members to apply a different set of cutting edges, or blade. An inner rotating member within a stationary outer cutting member provide cutting edges defined by cutting windows on the inner and outer cutting members, and a rotational drive applies an oscillating rotation such that one of the cutting windows, corresponding to one of the sets of cutting edges, engages an extraction region such as tissue or bone. The use of different sized cutting windows allows variance in the aggressiveness of the cut, and allows selection of another cutting window by rotating the cutting member to align the selected cutting window with the cutting edges on the other (inner or outer cutting member) for engagement with the extraction area.

Unfortunately, conventional approaches to arthroscopic extraction and control suffer from the shortcoming that conventional cutting instruments employ only a single blade or cutting surface engaged in a continuous rotary motion, thus applying the same cutting edge repeatedly on each rotation. Configurations herein are based, in part, on the observation that conventional cutting instruments employ only a single blade on each cutting member, therefore requiring extraction and reinsertion in order to attach a different blade with a different cut aggressiveness. It would be beneficial, therefore, to provide a dual set of separately engageable blades or cutting edges on the same instrument to avoid the need to withdraw an already inserted instrument and change cutting members to achieve a different cutting function.

Accordingly, configurations herein substantially overcome the shortcoming of repetitive instrument extraction and changeover by employing a cutting member having dual cutting functions from multiple sets of cutting edges engageable in an oscillating manner such that only one of the sets of cutting edges is active. The disclosed approach includes a method and apparatus to provide a resecting device using a standard rotary shaving system that combines effective resection of tough tissue (e.g. meniscus) with less aggressive resection for smoothing and debridement. Such a dual function arthroscopic blade as discussed below combines aggressive resection capability with less aggressive smoothing and debridement abilities within one single rotary shaving device.

In an example arrangement, two cutting windows on either the inner or outer cutting member each define a pair of cutting edges for slideably engaging a cutting window on the other cutting member for shearing engagement of the cutting edges. The rotation causes the two blade edges to pass in close tolerance with a shearing action, similar to a pair of scissors blades absent a pivoting hinge point. Each of the cutting windows therefore defines a pair of opposed cutting edges for engagement with the cutting edges on the other concentric cutting member. A drive mechanism applies oscillatory rotation sufficient to alternately engage the opposed cutting edges on each side of the cutting window with corresponding edges on the other cutting member, typically around a half revolution depending on the width of the respective cutting windows. In contrast, conventional approaches perform unidirectional rotation of at least a plurality of revolutions, thus repeatedly engaging a single cutting edge repeatedly before engaging the opposed edge, therefore permitting only a single cutting window and corresponding set of opposed cutting edges on a particular instrument.

Conventional arthroscopic cutting blade arrangements therefore suffer from the shortcoming that oscillatory or periodic rotation includes a plurality of complete rotations in one direction before reversing, thus permitting only a single cutting window and associated pair of cutting edges. In conventional approaches, the use of multiple cutting windows would cause each to be engaged upon each revolution, obviating selectivity of multiple windows. In the example arrangement, a more aggressive cut provided by a wider cutting window, and a less aggressive cut provided by a narrower cutting window allow alternate extraction of, for example, bone and soft tissue, using the same instrument without extraction and reinsertion. Selection of an alternate cut provided by another cutting window occurs by rotating the selected cutting window slightly more than a half rotation (in the case of a dual window) to bring the selected cutting window into alignment and simultaneously rotate the previously engaged cutting window to a dormant side away from the extraction area.

Typically, at least one of the inner and outer cutting members employs a single cutting window for focusing suction toward the extraction area without permitting stray suction through unused cutting windows. Further, having greater than two cutting windows tends to limit the cutting window size, and corresponding oscillatory motion range permitted by the different windows. For example, a third cutting window would allow each only approximately ⅓ of a revolution range of motion, therefore limiting the size of the corresponding cutting windows.

In further detail, the disclosed arthroscopic cutting instrument includes elongated cylindrical members including an inner member concentrically disposed within an outer member and adapted for rotation therewithin, such that each of the cylindrical members has a proximate end for engaging a drive mechanism and a distal end having at least one cutting edge. Each cutting edge is responsive to the rotation for causing slideable engagement with a cutting edge on the other cylindrical member (e.g. inner or outer), and in which at least one of the cylindrical members includes multiple cutting edges. Each of the multiple cutting edges is responsive to the oscillatory rotation for engagement with a selected subset of the multiple cutting edges during a particular oscillatory cycle. The oscillatory rotation disposes the cutting edges of the selected subset through a cutting range to repeatedly engage a cutting edge on the other member without engagement by cutting edges of an unselected subset, thus the unselected subset is defined by the cutting edges of the multiple cutting edges not in the selected subset, as now described further below.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

FIG. 5 shows an exploded view of the inner and outer cutting members of FIG. 4;

FIG. 6 shows an assembled view of the inner and outer cutting members of FIG. 5;

FIG. 13a shows a perspective view of the inner cutting member;

FIG. 13b shows an end view of the inner cutting member;

FIG. 13c shows a top view of the inner cutting member;

FIG. 13d shows a bottom or opposed view of the inner cutting member of FIG. 13c;

FIG. 13e shows a perspective view of the outer cutting member;

FIG. 13f shows a side view of the outer cutting member;

FIG. 13g shows an end view of the outer cutting member;

FIG. 13h shows a top view of FIG. 13f;

FIG. 13i shows a perspective cutaway view of the inner cutting member disposed within the outer cutting member;

FIG. 14a shows a perspective view of the inner cutting member;

FIG. 14b shows an end view of the inner cutting member;

FIG. 14c shows a top view of the inner cutting member;

FIG. 14d shows a side view of the inner cutting member;

FIG. 14e shows a perspective view of the outer cutting member;

FIG. 14f shows an end view of the outer cutting member;

FIG. 14g shows a top view of the outer cutting member;

FIG. 14h shows a bottom or opposed view of the outer cutting member of FIG. 14g; and FIG. 14i shows a perspective cutaway view of the inner cutting member disposed within the outer cutting member.

DETAILED DESCRIPTION

Depicted below is an example configuration of the arthroscopic instrument as disclosed and claimed herein. Configurations of the disclosed approach employ a concentric two tube construction without a rotatable shield and knob, thus reducing the cost, complexity and outside diameter of the precedent design. Functionality is enabled via selective oscillatory motion over a partial revolution of the inner member. In the disclosed arrangement, the arthroscopic instrument includes a pair of rotationally opposed cutting edges on each of an inner cutting member and an outer cutting member, such that the inner cutting member is disposed within the outer cutting member for rotational movement therewithin. The arthroscopic instrument is operable as a rotary shaving device having two different sized windows located on either the inner or outer blade combined with a single window located on the opposite blade (cutting member). The device is insertable into a motor drive unit which is controlled such that it oscillates substantially within a 180 degree operating range for oscillatory rotation such that only one of the cutting windows is employed within a particular oscillation pattern about half a rotation, depending on the size of the active cutting window. The semicircular oscillatory mode alternates rotation in substantially 180 degree increments and applies only one of multiple cutting windows on the cutting member.

Figure 1:
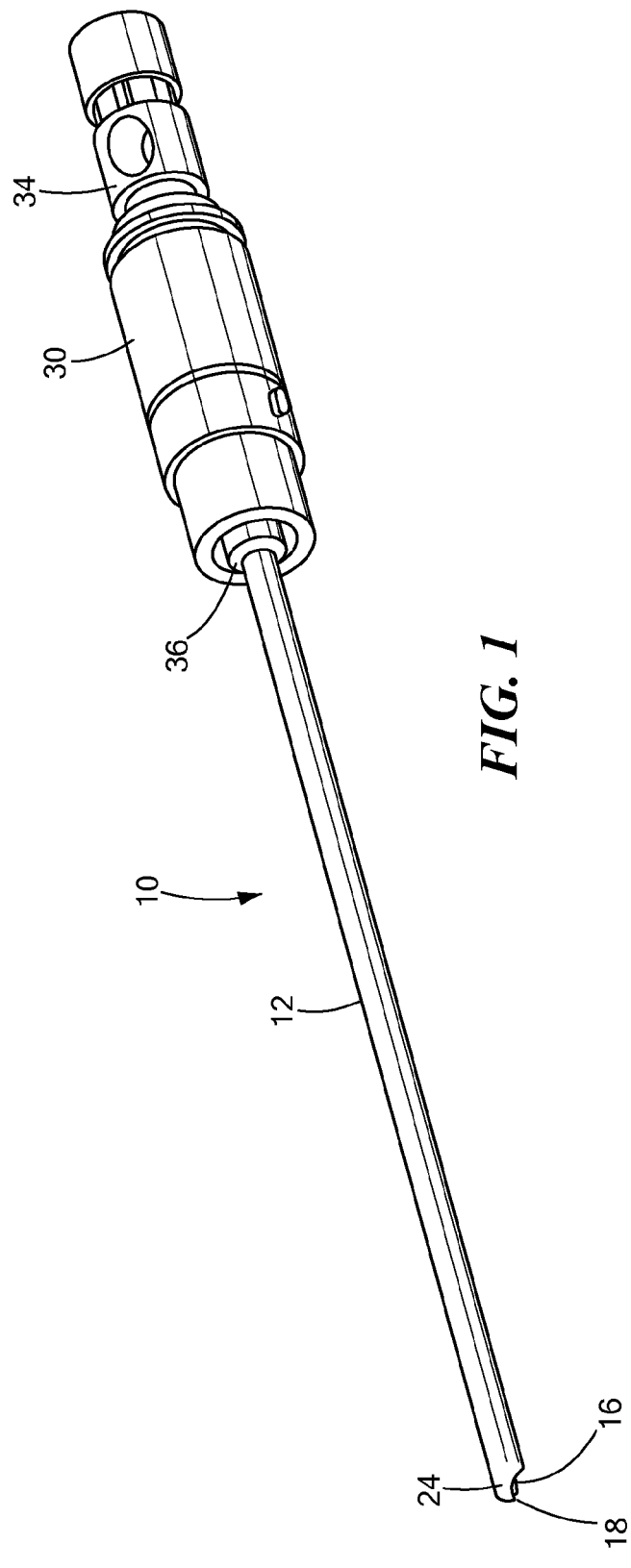
FIG. 1 is a perspective view of an arthroscopic instrument as disclosed herein.
Figure 2:
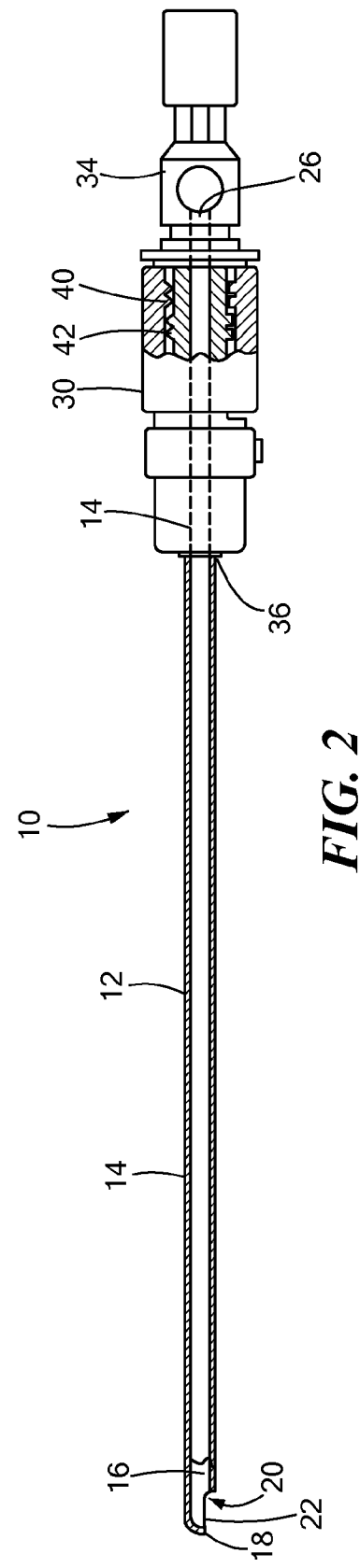
FIG. 2 is a side view of the arthroscopic instrument of FIG. 1.

FIG. 1 is a perspective view of an arthroscopic instrument as disclosed herein, and FIG. 2 is a side view of the arthroscopic instrument of FIG. 1. Referring to FIGS. 1 and 2, the arthroscopic surgical instrument 10 (instrument) includes a rigid, stationary outer cutting member 12, within which rotates a rigid inner cutting member 14 (shown partly in dotted lines in FIG. 2), and a dual function cutting portion, or blade 16, also formed as part of the inner cutting member 14. The distal end of the outer cutting member 12 defines at least one opening 18 through which the blade 16 is exposed. At least one other opening 20 is defined in the blade 16. The cutting edges 22 of the blade opening 20 cooperate with cutting edges 24 of the outer tube opening 18 to shear tissue and bone during operation of the instrument. In addition, the blade opening 20 aligns with the outer tube opening 18 periodically as the inner cutting member 14 rotates, thereby admitting tissue and bone fragments into the interior of the blade 16 and connected inner cutting member 14. These fragments are then removed by suction through a central opening 26 in the inner cutting member 14.

The instrument 10 further includes a hub 30 and a rotatable drive shaft 34. The proximal end of the outer cutting member 12 is rigidly mounted to the hub 30 at a sealed joint 36, while the proximal end of the inner cutting member 14 is mounted and sealed to the drive shaft 34, which rotates within the hub 30. The hub 30 and drive shaft 34 are secured in rotational communication by any suitable manner, such as short threaded portions 40 and 42, respectively, which, after being engaged and screwed past each other, serve as abutments to prevent the drive shaft from sliding back out of the cutting member. A snap fit or frictional resilient arrangement may be used instead of the threads to accomplish the same goal.

Figure 3:
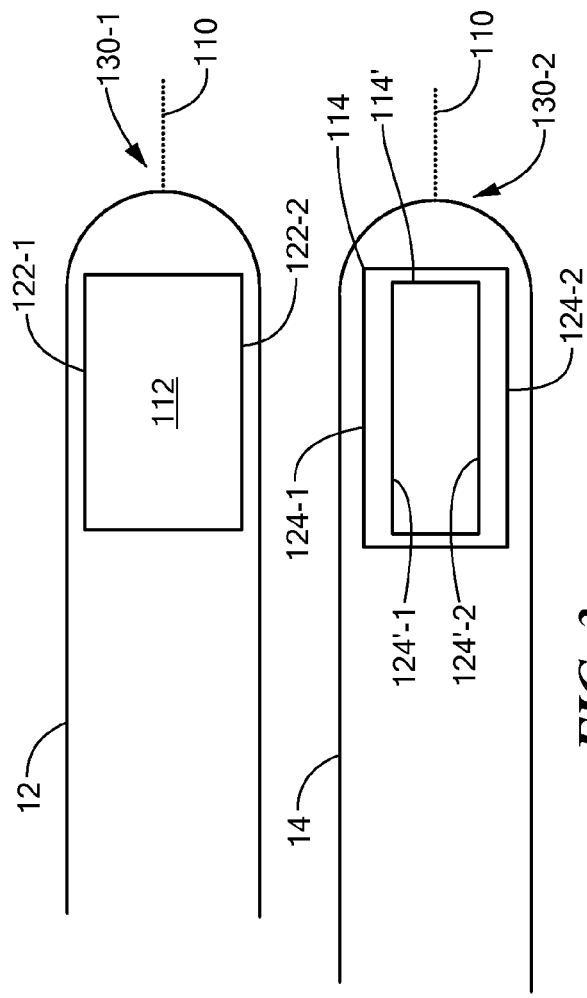
FIG. 3 shows the cutting windows of the inner and outer cutting members in the instrument of FIG. 2.

FIG. 3 shows cutting windows 112, 114, 114' of the inner 14 and outer 12 cutting members in the instrument 10 of FIG. 2. Referring to FIG. 3, both the inner cutting member 14 and the outer cutting member 12 have a cutting window 112 and 114, and at least one of the cutting members 12,14 has at least one other cutting window 114' (shown on the inner cutting member 14 in FIG. 3). Each of the cutting windows 112, 114, 114' define opposed cutting edges 122-1, 122-2 (122 generally) and 124-1, 124-2 (124 generally) formed parallel to an axis 110 of rotation, as well as alternate cutting window 114', having cutting edges 124'-1, 124'-2 (124' generally). Each of the cutting windows 122, 124 and 124' are formed as generally rectangular oriented lengthwise along the axis 110 so as to maximize the cutting edges 122, 124 and are formed by any suitable method, such as by cutouts from a closed tube along lines parallel and perpendicular to the axis 110. In alternate arrangements, discussed further below, the cutting windows 122, 124 and 124' may extend to a closed end 130-1, 130-2 (130 generally).

Figure 4:
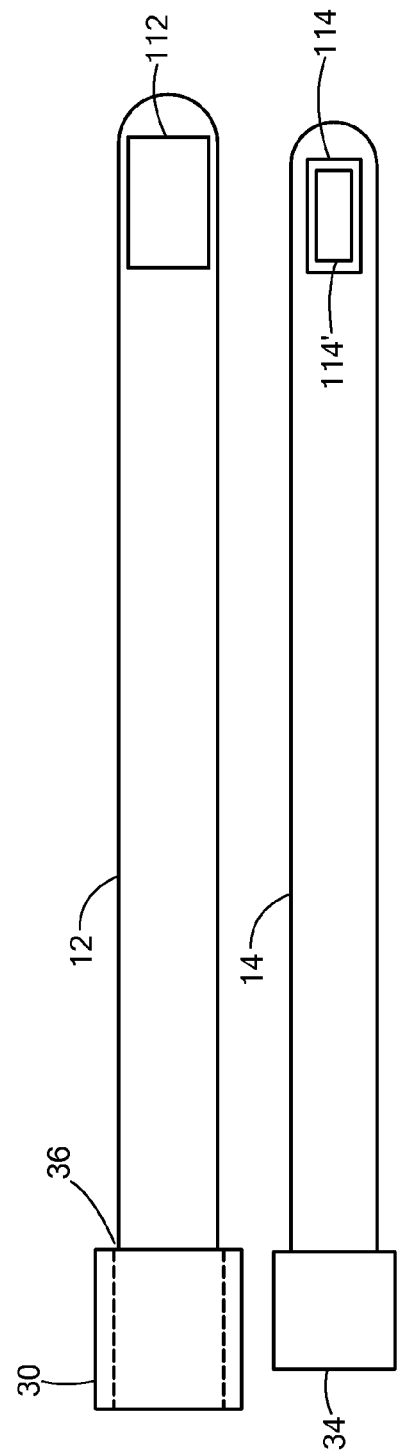
FIG. 4 shows the inner and outer cutting members in the instrument of FIG. 3.

FIG. 4 shows the inner and outer cutting members in the instrument of FIG. 3. Referring to FIGS. 3 and 4, the inner 14 and outer 12 cutting members extend from the drive shaft 34 and hub 30, respectively for rotational communication. The drive shaft 34 engages a drive mechanism for oscillating rotation within the hub 30, thus rotating the inner cutting member 14 within the outer cutting member 12. Rotation of the drive shaft 34 causes the cutting edges 124, 124' of the inner cutting member 14 to engage the cutting edges 122 of the outer cutting member in a slideable or shearing manner for cutting tissue and/or bone at an extraction area defined by placement of the window 112 of the outer cutting member 12 in a surgical field.

Upon rotational movement by the inner cutting member 14, a first cutting edge 124-1 of the inner cutting member 14 engages a first cutting edge 122-2 of the outer cutting member 12, and a second cutting edge 124-2 of the inner cutting member 14 engages the second cutting edge 122-1 of the outer cutting member 12 in an alternating manner. An oscillatory drive pattern of substantially 180 degrees drives the alternating manner of cutting in which only one of the dual cutout windows 114, 114' is employed as a cutting member during the semirotational oscillation of substantially about 180 degrees. Such semicircular rotation ensures that only one cutting window 114 and associated pair of cutting edges 124 engages the extraction area.

In one conventional approach, U.S. Pat. No. 4,834,729 ('729), assigned to the assignee of the present application, an arthroscopic surgical instrument includes an outer stationary member having a distal aperture, the wall of the outer member defining a first cutting edge at the aperture, and an internal movable member disposed within the outer member, adapted to be power driven and having a second cutting edge arranged to move toward and closely past the first cutting edge in rapid, repetitive fashion to sever tissue. However, the '729 disclosure employs unidirectional rotary motion, thus engaging the extraction surface from a single direction, in contrast to the oscillatory rotation disclosed herein.

Another conventional approach is discussed in U.S. Publication No. 2007/0282361 ('361), which suggests that a cutting instrument can be used in both directions of rotation and oscillating, however no further clarification of oscillatory drive are disclosed or claimed. There is no disclosure of an oscillation mode which alternates rotational movement in increments substantially less than a full rotation, such as 180 degrees, or rotation that alternately engages opposes cutting members of the same window, as conventional methods typically oscillate multiple full rotations in one direction before reversing, thereby engaging cutting members of one side of a window multiple times before engaging the opposed side.

Further, the '361 publication shows a welded forward tip, rather than unitary composition with the tubular member, and has an angular cutaway that defines a cutaway opening extending at an angle from the annular surface parallel to the axis of rotation to a point substantially around the center of the head, or tip. In the present application, in contrast, the cutting surfaces are formed from a cutting window defined by a cut parallel to the axis of rotation, rather than angular toward the tip.

U.S. Pat. No. 5,766,199 suggests a dual window structure of an inner member, however a corresponding cutting edge of an outer member extends through the rotational axis. Further, the disclosed curvilinear window periphery has edges of differing included angles, and employs cutting windows that extend through the cutting member causing discontinuity at the tip because the cutting windows open at the distal tip thereby producing a distal end slot having adjacent finger ends with low included angle cutting edges. In contrast, the claimed approach defines the cutting edges substantially parallel to the rotational axis, and the cutting windows do not extend through the axis nor through the tip to form a discontinuous surface with "finger ends," in a so-called "open mouth" arrangement.

FIG. 5 shows an exploded view of the inner and outer cutting members of FIG. 4. Referring to FIGS. 4 and 5, the inner cutting member 14 has a slightly smaller diameter Di that diameter Do of the outer cutting member 12 such that it is adapted for slideable insertion and rotation within the outer cutting member 12 within a sufficiently close tolerance that slideable engagement during rotation causes a shearing action as the cutting edges 122, 124 engage.

FIG. 6 shows an assembled view of the inner 14 and outer 12 cutting members of FIG. 5. Referring to FIGS. 5 and 6, upon insertion of the inner cutting member 14 concentrically into the outer cutting member 12, the cutting window 114 aligns with the cutting window 112, such that oscillatory rotation of the inner cutting member 114 causes the cutting edges 124-1 and 124-2 to slideably engage the cutting edges 122-1 and 122-2. Further, upon rotation of the inner cutting member 14 about half a revolution, the cutting window 114' aligns with the cutting window 112, such that further oscillation causes the cutting edges 124'-1 and 124'-2 to engage the cutting edges 122-1 and 122-2. Varying a width 115, 115' of the cutting windows 114, 114' effects the aggressiveness of the cut resulting from oscillating, with a larger width generally resulting in a more aggressive cut. Sharpening or modifying (such as by serrations or "teeth") of the cutting edges 122, 124 also effects the cut.

Figure 7:
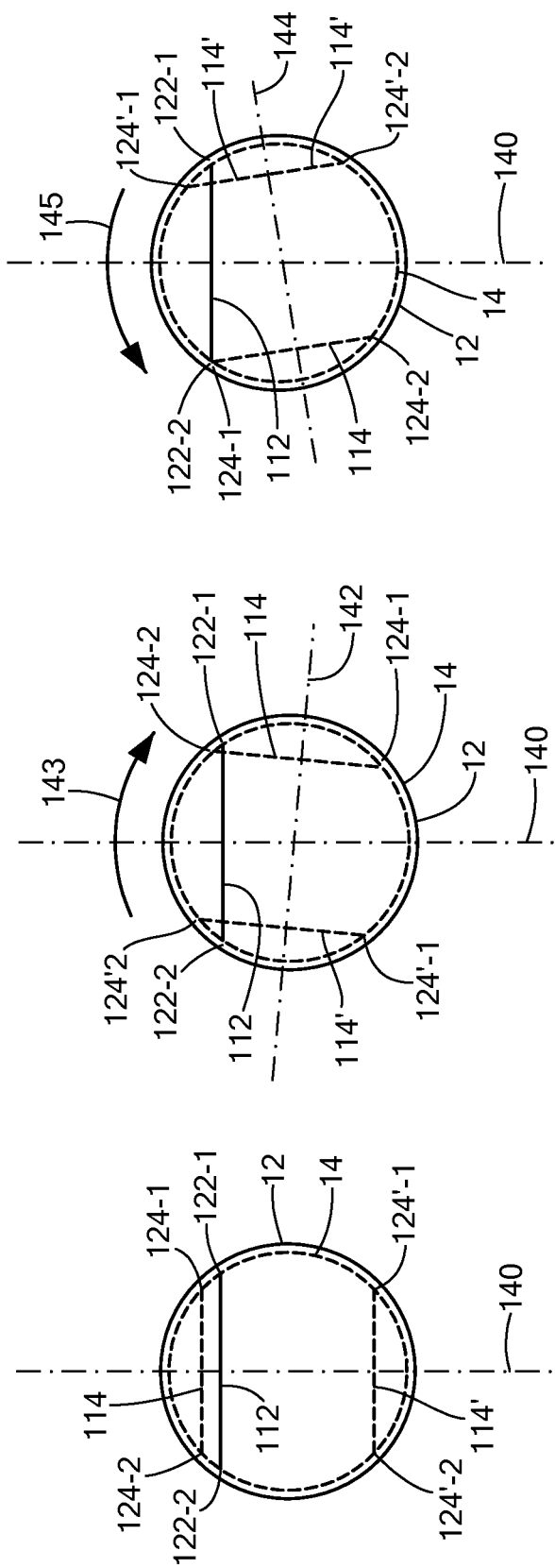
FIG. 7 shows a cutaway view of the operation of the inner and outer cutting members of FIG. 6.

FIG. 7 shows a cutaway view of the operation of the inner 14 and outer 12 cutting members of FIG. 6. Referring to FIGS. 6 and 7, an oscillatory cycle of oscillatory rotation of the inner cutting member 14 of FIG. 6 is shown in FIG. 7. A stationary axis position 140 (normal to cut axis 110) shows the inner cutting member 14 at rest with the cutting window 114 aligned with the cutting window 112, and the cutting window 114' opposed, as shown by the stationary (rest) axis position 140. Upon an idle or stationary state, the cutting edges 122-1 and 122-1 (on outer cutting member 12) align substantially with and parallel to the cutting edges 124-1 and 124-2 (inner cutting member 14). Rotating along the cutting axis 180 degrees results in similar alignment with respect to cutting edges 124'-1, 124'-2.

During oscillation, rotation of the inner cutting member 14 as shown by arrows 143 and 145 through a oscillation range defined by a set of range limits 142 and 144, shown by arrows 143 and 145 respectively, disposes the cutting edge 124-2 to engage the cutting edge 122-1 from rotation substantially around the range limit 142, and on a reverse oscillation (145) to engage the cutting edge 124-1 with the cutting edge 122-2. Selection of cutting window 124' includes rotation to align the cutting window 114' with 112, and oscillation of cutting edges 124'-1 with 122-1 and 124'-2 with 122-2.

Figure 8:
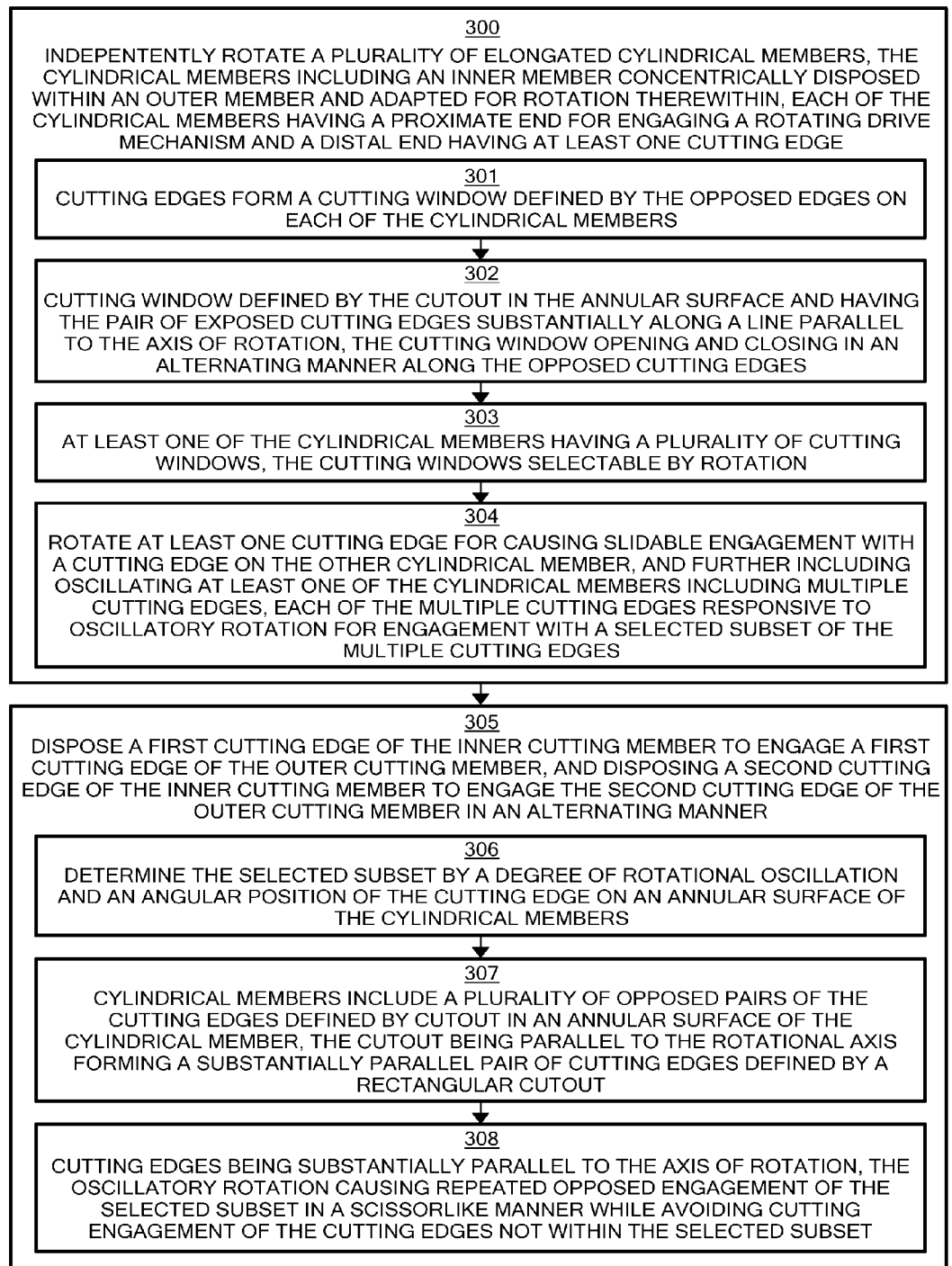
FIGS. 8 and 9 show a flowchart of selection and control of the dual function arthroscopic instrument of FIG. 7.
Figure 9:
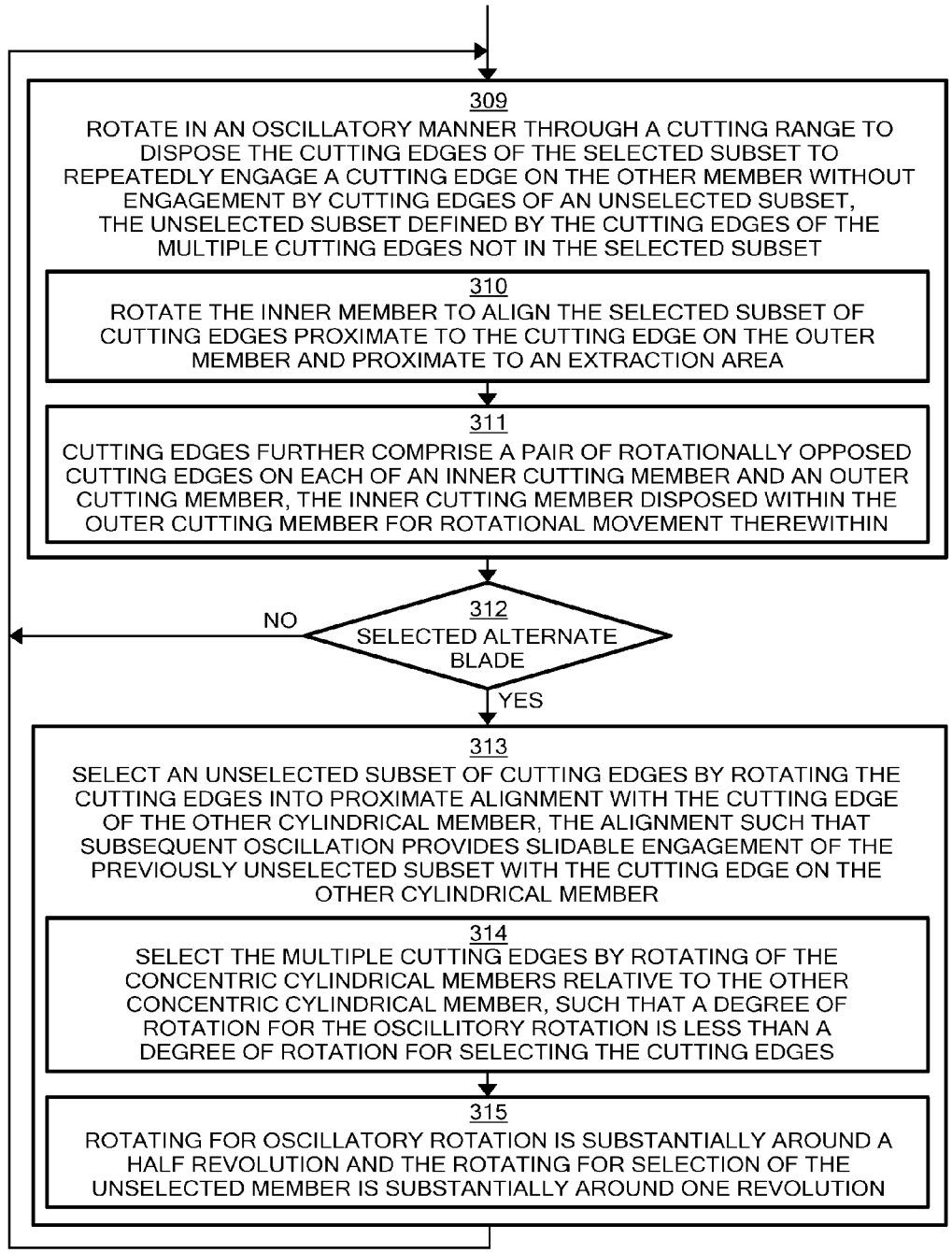

FIGS. 8 and 9 show a flowchart of selection and control of the dual function arthroscopic instrument of FIG. 7. Referring to FIGS. 4-9, the drive shaft 34 imparts oscillation and selection control to the inner cutting member 14. Accordingly, the method for controlling a surgical cutting instrument 10 as disclosed herein includes independently rotating a plurality of elongated cylindrical members 12, 14, the cylindrical members including an inner member 14 concentrically disposed within an outer member 12 and adapted for rotation therewithin, such that each of the cylindrical members 12, 14 has a proximate end for engaging a rotating drive mechanism and a distal end 130 having at least one cutting edge 122, 124, as depicted at step 300. The cutting edges 122, 124 form cutting windows 112, 112' (FIG. 10 below), 114 and 114' defined by the opposed edges on each of the cylindrical members 12, 14, as disclosed at step 301. In the example arrangement, the cutting windows 112, 114 are defined by the cutout in the annular surface of the cutting members 12, 14, such that the cutting windows each 112, 114 have a pair of opposed cutting edges 122-1, 122-2, 124-1, 124-2 substantially along an line parallel to the axis of rotation 110, in which the cutting windows 112, 114 are configured for opening and closing in an alternating manner along the opposed cutting edges 122, 124, as depicted at step 302. At least one of the cylindrical members 12, 14 has a plurality of cutting windows 114, 114', such that the cutting windows 114, 114' are selectable by rotation of the inner cutting member 14, as shown at step 303. Rotating in this manner includes rotating at least one cutting edge 122, 124 for causing slideable engagement with a cutting edge 122, 124 on the other cylindrical member 12 or 14, and further including oscillating at least one of the cylindrical members 12, 14 including multiple cutting edges, in which each of the multiple cutting edges 122, 124 is responsive to oscillatory rotation for engagement with a selected subset of the multiple cutting edges 122, 124, as depicted at step 304. In the example shown in FIG. 4, the selected subset is either 124-1, 124-1, or 124'-1, 124'-2, depending on which cutting window 114 or 114' is aligned with the cutting window 112 on the outer cutting member 12.

In the example arrangement, the arthroscopic cutting blade is inserted to an extraction area of a surgical site, typically as one of several instruments similarly suited for surgical activity. The drive shaft 34 rotates to dispose a first cutting edge 124-2 of the inner cutting member 14 to engage a first cutting edge 122-1 of the outer cutting member 12, and disposes a second cutting edge 124-1 of the inner cutting member 14 to engage the second cutting edge 122-2 of the outer cutting member in an alternating manner, as disclosed at step 305. Upon initial insertion, rotation of the drive shaft 34 determines the selected subset (e.g. 114 or 114') by a degree of rotational oscillation and an angular position of the cutting edge 124, 124' on an annular surface of the cylindrical members 14, as depicted at step 306. Initial rotation will bring the cutting member having the multiple cutting windows (14 shown) into alignment with the other cutting member having a single window (12 in the example shown). Thus, at least one of the cylindrical members 14 includes a plurality of opposed pairs (124-1, 124-2 and 124'-1, 124'-2) of the cutting edges defined by a cutout 114 and 114' in an annular surface of the cylindrical member 14, such that the cutout is longitudinally parallel to the rotational axis 110 forming a substantially parallel pair of cutting edges defined by the rectangular cutout, as shown at step 307. This orientation provides that the cutting edges 124 are substantially parallel to the axis of rotation 110, in which the oscillatory rotation causes repeated opposed engagement of the selected subset in a shearing manner while avoiding cutting engagement of the cutting edges not within the selected subset, as depicted at step 308.

Following initial selection of the cutting window 124 or 124', the drive shaft 34 rotates in an oscillatory manner through the cutting range 142, 144 to dispose the cutting edges 124 of the selected subset to repeatedly engage a cutting edge 122 on the other member 12 without engagement by cutting edges of an unselected subset such that the unselected subset is defined by the cutting edges of the multiple cutting edges not in the selected subset, e.g. the complement of the set 124 or 124', as depicted at step 309. Oscillation includes rotating the inner member 14 to align the selected subset of cutting edges 124, 124' proximate to the cutting edge 122 on the outer member 12 and proximate to an extraction area, as disclosed at step 310. In the example arrangement shown, the cutting edges further comprise a pair of rotationally opposed cutting edges 124, 122 on each of an inner cutting member 14 and an outer cutting member 12, such that the inner cutting member 14 is disposed within the outer cutting member 12 for rotational movement therewithin, as depicted at step 311. The oscillating by the hub 34 therefore repeatedly engages the cutting edges 124 of the selected window 114 (or edges 124' when cutting window 114' is selected) with the cutting edges on the other (e.g. outer 12) member in a shearing manner for cutting bone and tissue while the unselected (e.g. 124') window remains unengaged from the edges 122 of cutting window 112 during the oscillation.

Oscillation continues until selection of an alternate cutting window 114' and associated cutting edges 124' (blade), as shown at step 312. In response to operator control, the drive shaft 34 selects an unselected subset (124' in the example shown) of cutting edges by rotating the cutting edges 124' into proximate alignment with the cutting edge 122 of the other cylindrical member 12, the alignment such that subsequent oscillation provides slideable engagement of the previously unselected subset with the cutting edge 122 on the other cylindrical member 12, as depicted at step 313. This includes selecting the multiple cutting edges 124 or 124' by rotating of the concentric cylindrical member 14 relative to the other concentric cylindrical member 12, such that a degree of rotation for the oscillatory rotation is less than a degree of rotation for selecting the cutting edges, as shown at step 314 and FIG. 7. An oscillatory rotation causes the inner member 14 to travel through the range defined by limits 142,144, while a blade selection (as in step 312) rotates the cutting window 114' substantially in alignment with the cutting window 112, for continued oscillation using the newly selected cutting edges 124'. Thus, rotation for oscillatory rotation is substantially around a half revolution and the rotating for selection of the unselected window 114' is substantially around one revolution from a range limit (142 or 144) of the previously selected window 114, as depicted at step 315.

Figure 10:
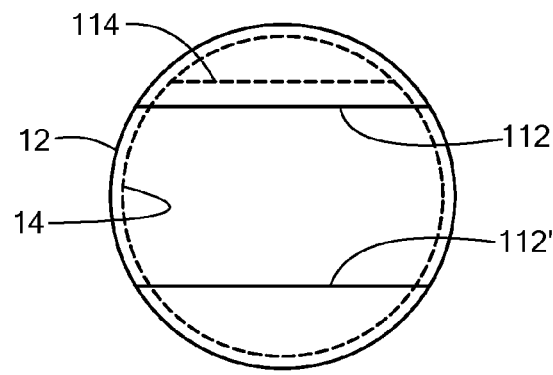
FIG. 10 shows an alternate configuration having a dual window on the outer cutting member.

FIG. 10 shows an alternate configuration having a dual window on the outer cutting member 12 and a single cutting window 114 on the inner cutting member 14. A plurality of cutting windows 112, 112' on the outer cutting member 12 provides that selection of the cutting window occurs by rotating the outer cutting member 12, typically the cutting member affixed to the base 30. Alternatively, an opposed surface of an extraction area may be accessed more readily from the second cutting window 112'. As with the dual window on the inner cutting member, different sized windows 112, 112' allows varying aggressiveness of cut by invoking different windows. It should be noted that by having a single window 112 or 114 on at least one of the cutting members 12, 14, suction applied via the base 30 is focused only on the extraction site for evacuating cut tissue or bone. Multiple windows on each of the inner 14 and outer cutting member 12 would result in the extractive suction force being directed to both openings.

Figure 11:
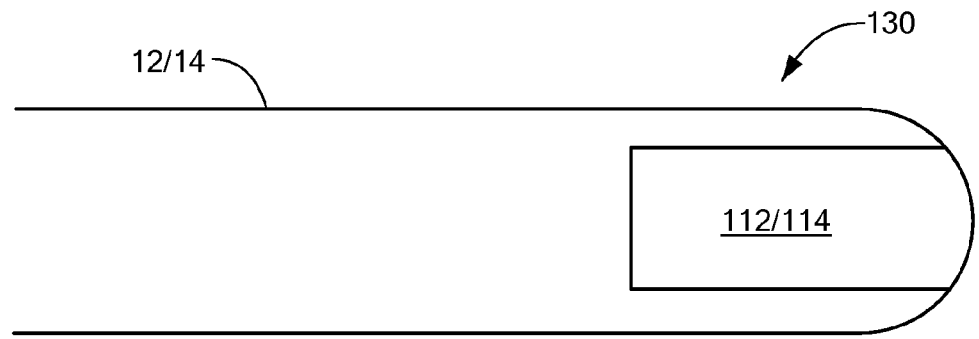
FIG. 11 shows an alternate configuration extending the cutting window on an inner or outer cutting member as in FIG. 3.
Figure 12:
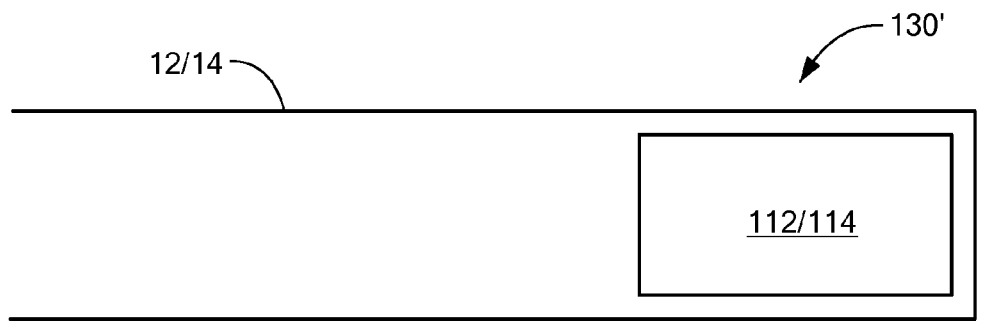
FIG. 12 shows an alternate configuration of the closed end of the inner or outer cutting member as in FIG. 3.

FIG. 11 shows an alternate configuration extending the cutting window on an inner 14 or outer cutting member 12 as in FIG. 3. Referring to FIGS. 3 and 11, the substantially rectangular cutting windows 112 and 114 may be formed by a cut extended to the tip 130 of the cutting member 12, 14. Similarly, FIG. 12 shows an alternate configuration of the closed end of the inner or outer cutting member as in FIG. 3. Referring to FIG. 12, the tip 130 may be squared off 130' or may be formed in various combinations of flattened or convex formations. As with the aperture formed by the cutting windows 112, 114, a closed end 130, 130' allows suctional force to focus on the windows for extracting cut material.

FIGS. 13a-13i show views of a dual inner window configuration as depicted in FIGS. 3-7. Referring to FIGS. 6 and 13a-13i, FIG. 13a shows a perspective view of the inner cutting member 14 having dual cutting windows 114 and 114' of varying widths 115 and 115' respectively. The cutting window 114 defines cutting edges 124-1 and 124-2, and the smaller cutting window 114' defines cutting edges 124'-1 and 124'-2.

Figure 13A:
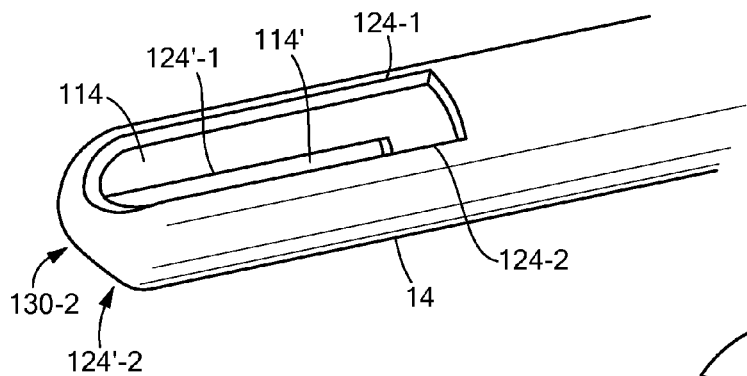
FIGS. 13a-13i show views of a dual inner window configuration.
Figure 13B:
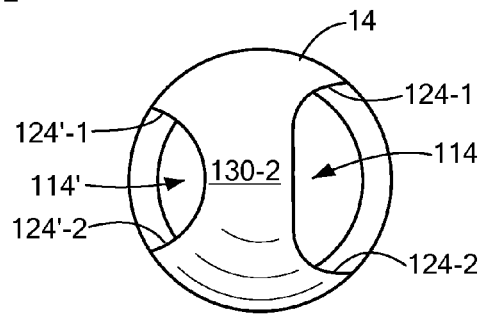
Figure 13C:
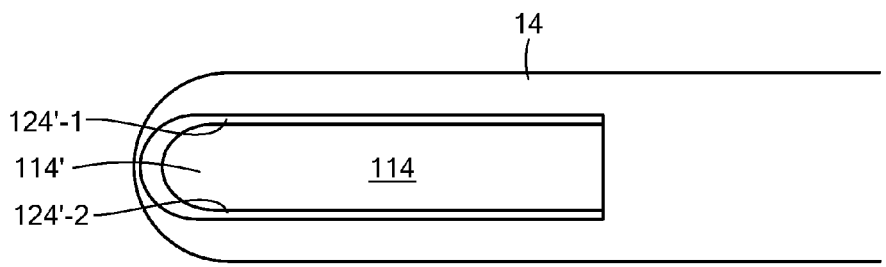
Figure 13D:
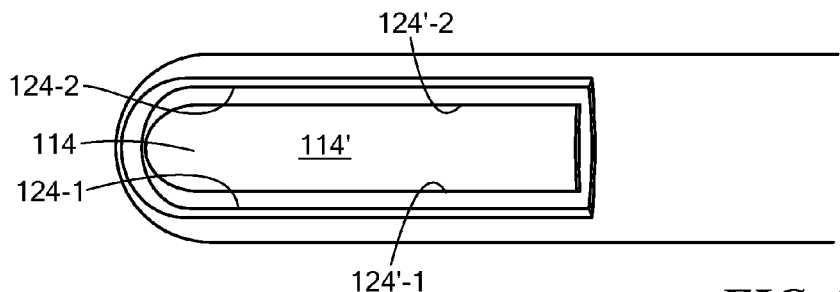

FIG. 13b shows an end view of the inner cutting member 14 having cutting windows 114, 114' and cutting edges 124-1, 124-2, 124'-1, 124'-2. The tip 130 is defined by a concave end as in FIG. 11 and linear cutaway extending to the tip 130. FIG. 13c shows a top view of the inner cutting member 14 with cutting window 114' in above cutting window 114 and obscuring the cutting edges 124-1, 124-2 of the larger cutting window 114. FIG. 13d shows a bottom or opposed view of the inner cutting member of FIG. 13c, such that cutting edges 124-1 and 124-2 of window 114 are visible in the foreground and cutting edges 124'-1 and 124'-2 beyond.

Figure 13E:
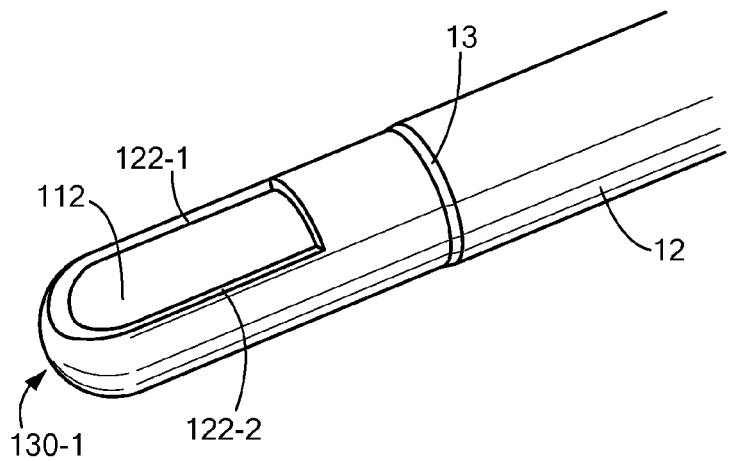

FIG. 13e shows a perspective view of the outer cutting member 12 having a single cutting window 112 defining cutting edges 122-1 and 122-2. FIG. 13f shows a side view of the outer cutting member 12 with a reducing section 13 for altering the diameter for rotational communication with the inner portion 14. The reducing section may also represent a welded or attachment section for securing a separately fabricated windowed portion. Alternatively, unitary construction may be employed. The view shows the cutting window 112 and cutting edge 122-2 in the foreground obscuring distal cutting edge 122-1.

Figure 13G:
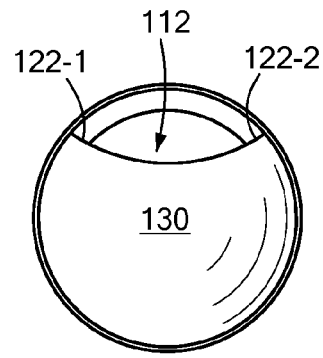
Figure 13F:
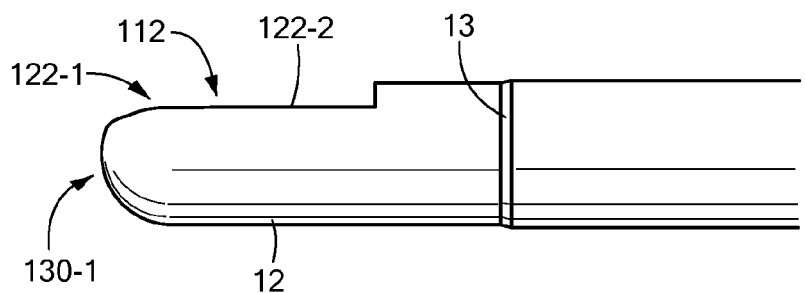
Figure 13H:
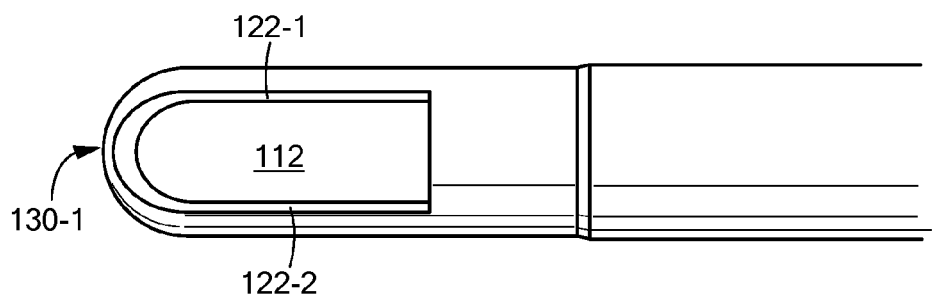
Figure 13I:
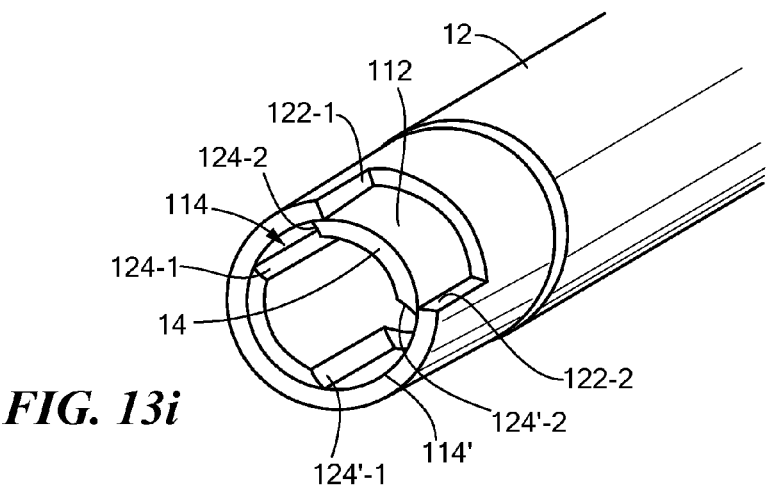

FIG. 13g shows an end view of the outer cutting member 12 with the cutting edges 122-1 and 122-2 defined by a concave cutout extending to the tip 130-1 as in FIG. 11 to define the cutting window 112. FIG. 13h shows a top view of FIG. 13f, and FIG. 13i shows a perspective cutaway view of the inner cutting member disposed within the outer cutting member 12 and the inner cutting member 14 rotated approximately ¼ turn out if alignment of the cutting windows 112 and 114.

Figure 14A:
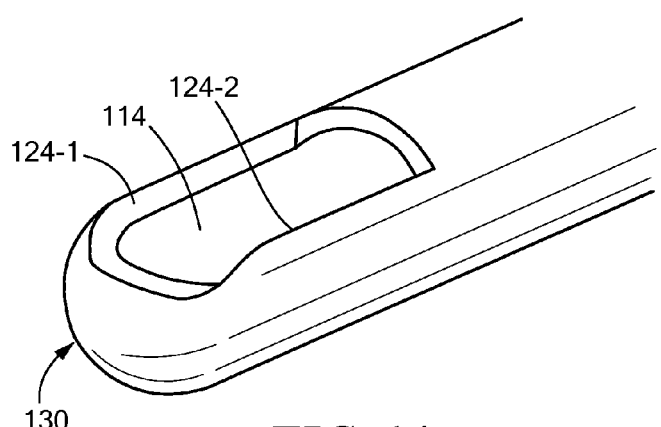
FIGS. 14a-14i show views of a dual outer window configuration.
Figure 14B:
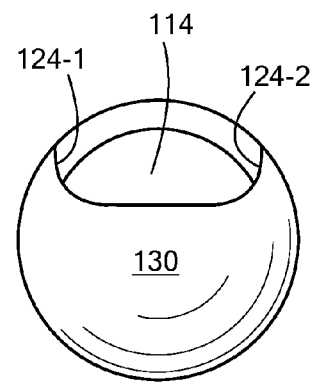
Figure 14C:
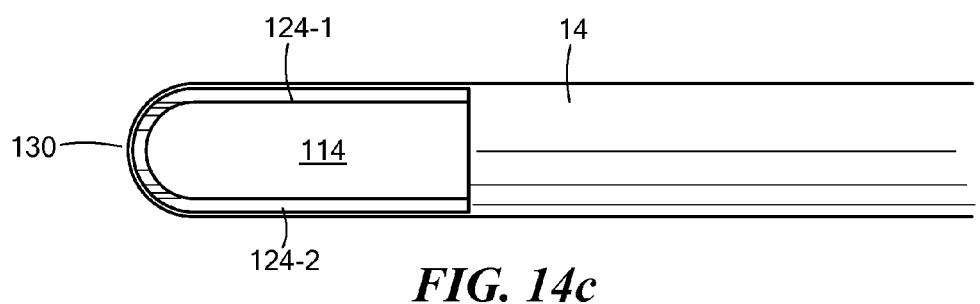
Figure 14D:
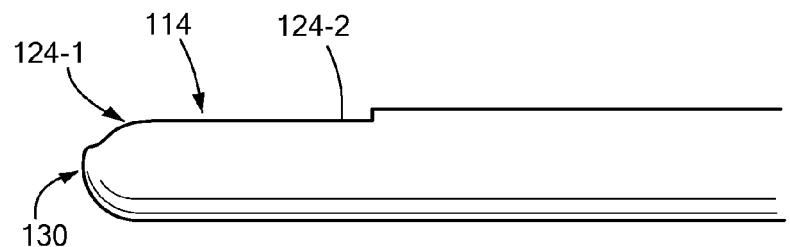

FIGS. 14a-14i show views of a dual outer window configuration as in FIG. 10. Referring to FIGS. 6 and 14a-14i, FIG. 14a shows a perspective view of the inner cutting member 14 having a single cutting window 114 and cutting edges 124-1, 124-1. FIG. 14b shows an end view of the inner cutting member 14 and cutting edges 124-1, 124-2. FIG. 14c shows a top view of the inner cutting member 14 and single cutting window 114. FIG. 14d shows a side view of the inner cutting member 14 defined by a cutaway forming cutting edges 124-1, 124-2 extending to the tip 130.

Figure 14E:
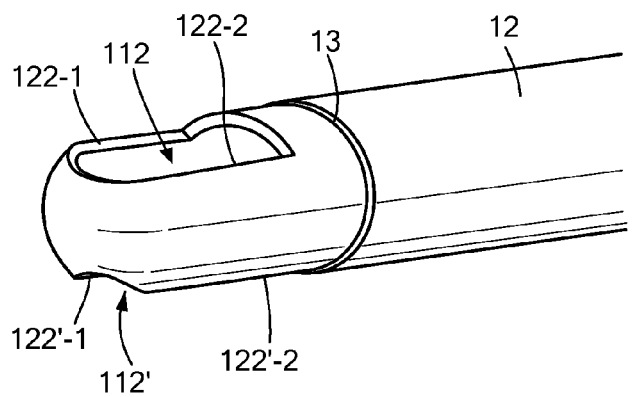
Figure 14F:
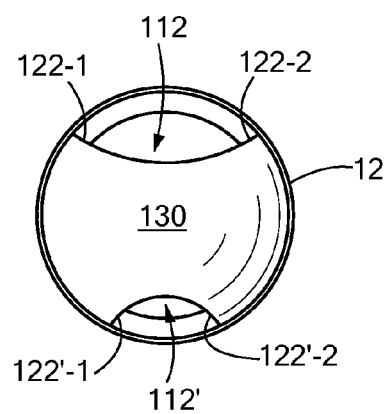
Figure 14G:
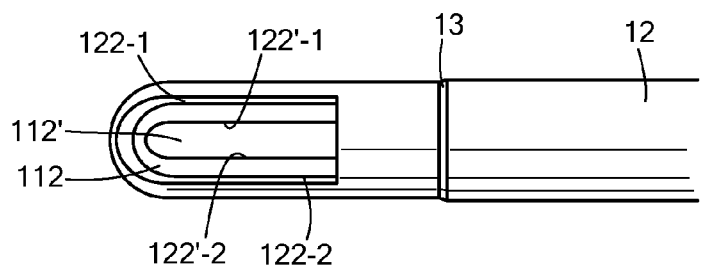
Figure 14H:
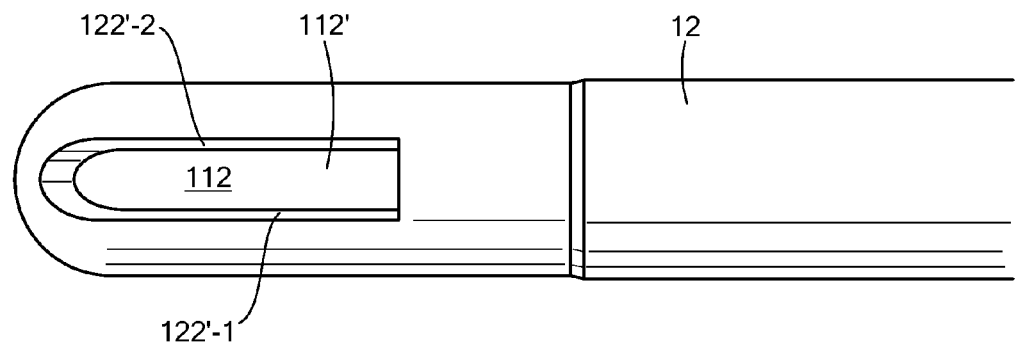
Figure 14I:
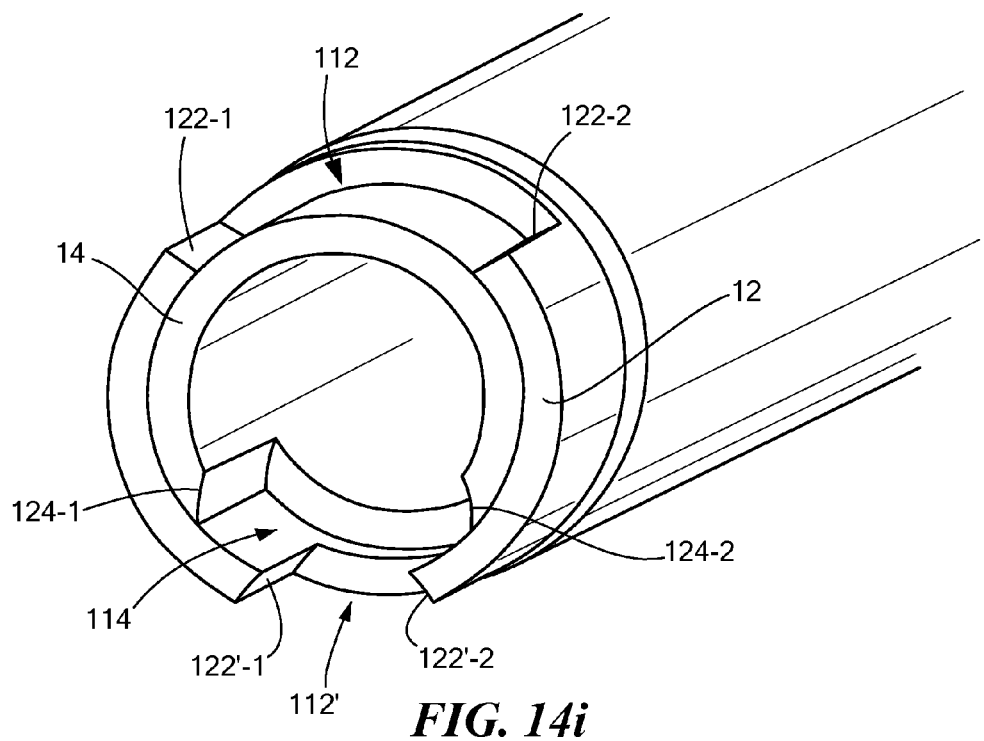

FIG. 14e shows a perspective view of the outer cutting member 12 having dual outer cutting windows 112 and 112' defining cutting edges 122-1, 122-2 and 122'-1, 122'-2, respectively. A reducing section 13 specializes adjustment or attachment of the cutting portion for rotation of the inner cutting member 14 therewithin. FIG. 14f shows an end view of the outer cutting member 12, and FIG. 14g shows a top view of the outer cutting member 12. The smaller width 115' cutting window 112' is visible through the larger width 115 cutting window 112, as are the cutting edges 122'-1, 122'-2, as well as cutting edges 122-1 and 122-2. FIG. 14 h shows a bottom or opposed view of the outer cutting member of FIG. 14g, showing cutting window 112' and cutting edges 122'-1, 122'-2 obscuring distal cutting edges 122-1, 122-2 defined by cutting window 112. FIG. 14i shows a perspective cutaway view of the inner cutting 14 member disposed within the outer cutting member 12 and adapted for rotational communication therewithin. Upon oscillating rotation as disclosed above, the cutting edges 122-1, 122-2 or 122'-1, 122'-2 alternately engage the cutting edges 124-1, 124-2 in a shearing action for extraction of bone and tissue fragments.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting, the full scope rather being conveyed by the appended claims.

What is claimed is:

1. An arthroscopic cutting instrument comprising:
   elongated cylindrical members, the cylindrical members including an inner member for engaging a drive mechanism and concentrically disposed within an outer member and adapted for rotation therewithin, each of the cylindrical members having a proximate end and a distal end having at least one cutting edge;
   each cutting edge responsive to the rotation for causing slideable engagement with a cutting edge on the other cylindrical member; and
   the inner members including multiple rotationally opposed windows, each cutting window including subsets of the cutting edges, each of the subsets defined by opposed cutting edges of the cutting window, each of the multiple cutting windows responsive to oscillatory rotation for engaging a selected subset of the cutting edges corresponding to a selected cutting window with the cutting edges on the outer member,
   the oscillatory rotation disposing the cutting edges of the selected cutting window through a cutting range to repeatedly engage a cutting edge on the outer member without engagement by cutting edges of an unselected cutting window,
   an alternate cut being defined by a width of the cutting window, such that a wider cutting window corresponds to a more aggressive cut than a narrower cutting window width.

2. The instrument of claim 1 wherein the selected subset is defined by rotating the inner member to align the selected subset of cutting edges proximate to the cutting edge on the outer member and proximate to an extraction area.

3. The instrument of claim 2 wherein the selected subset is determined by a degree of rotational oscillation and an angular position of the cutting edge on an annular surface of the cylindrical members.

4. The instrument of claim 1 wherein, each cutting window having opposed pairs of the cutting edges defined by a cutout in an annular surface of the cylindrical member, the cutout being parallel to the rotational axis forming a substantially parallel pair of cutting edges defined by a substantially rectangular cutout formed from a cut parallel to the axis from the distal end.

5. The instrument of claim 4 wherein the plurality of opposed pairs define different sized cutouts having cutting edges opposed by different distances for cutting at differing rates in response to oscillatory rotation.

6. The instrument of claim 5 wherein the cutting edges are substantially parallel to the axis of rotation, the oscillatory rotation causing repeated opposed engagement of the selected subset in a shearing manner while avoiding cutting engagement of the cutting edges not within the selected subset.

7. The instrument of claim 6 wherein an unselected subset of cutting edges is selectable by rotation into proximate alignment with the cutting edges of the outer member, the alignment such that subsequent oscillation provides slideable engagement of the previously unselected subset with the cutting edges on the outer member.

8. The instrument of claim 6 wherein cylindrical members have a closed end for directing a suctional force from the proximate end to evacuate material through the rectangular cutout.

9. The instrument of claim 1 wherein opposed pairs of the cutting edges each form the cutting window on each of the cylindrical members,
the cutting window defined by the cutout in the annular surface, the cutting window having the pair of opposed cutting edges substantially along a line parallel to the axis of rotation, the cutting window opening and closing in an alternating manner along the opposed cutting edges; and
wherein the cutting windows are selectable by rotation.

10. The instrument of claim 9 further comprising:
a pair of the rotationally opposed cutting edges disposed on each of the inner member and the outer member, the inner member disposed within the outer member for rotational movement therewithin; and
the rotational movement disposing a first edge of the inner member to engage a first edge of the outer member, and disposing a second edge of the inner member to engage the second edge of the outer member in an alternating manner.

11. The instrument of claim 10 wherein each of the multiple cutting edges is selectable from rotation of the inner member relative to the outer member, such that a degree of rotation for the oscillatory rotation is less than a degree of rotation for selecting the cutting edges.

12. The cutting instrument of claim 1 further wherein each cutting window includes similar opposed cutting edges.

13. The cutting instrument of claim 1 wherein the multiple cutting windows includes two cutting windows, each cutting window having opposed sets of cutting edges, each of the opposed sets operable for the alternate cut.

14. A surgical cutting instrument comprising:
a plurality of elongated cylindrical members adapted for independent rotation, the cylindrical members including an inner member for engaging a rotating drive mechanism concentrically disposed within an outer member and adapted for rotation therewithin, each of the cylindrical members having a proximate end and a distal end having at least one cutting edge;
at least one cutting edge responsive to rotation for causing slideable engagement with a cutting edge on the other cylindrical member;
the inner member including multiple rotationally opposed cutting windows, each cutting window including subsets of the cutting edges, each of the subsets defined by opposed cutting edges of the cutting window, each of the multiple cutting windows having cutting edges responsive to oscillatory rotation for engaging a selected subset of the cutting edges corresponding to a selected cutting window with the cutting edges the outer member,
the oscillatory rotation disposing the cutting edges of the selected cutting window through a cutting range to repeatedly engage a cutting edge on the outer member without engagement by cutting edges of an unselected cutting window,
an alternate cut being defined by a width of the cutting window, such that a wider cutting window corresponds to a more aggressive cut than a narrower cutting window width.

* * * * *